(12) United States Patent
Türker et al.

(10) Patent No.: US 7,287,561 B2
(45) Date of Patent: *Oct. 30, 2007

(54) FILLING SYSTEM FOR AN ANESTHETIC EVAPORATOR

(75) Inventors: Ahmet Türker, Lübeck (DE); Dirk-Stefan Reichert, Lübeck (DE); Claus Bunke, Sereetz (DE)

(73) Assignee: Dräger Medical AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/253,540

(22) Filed: Oct. 19, 2005

(65) Prior Publication Data

US 2006/0130930 A1 Jun. 22, 2006

(30) Foreign Application Priority Data

Dec. 21, 2004 (DE) .................. 10 2004 063 883

(51) Int. Cl.
*B65B 1/04* (2006.01)

(52) U.S. Cl. ...................................... 141/351; 141/367

(58) Field of Classification Search ............... 141/2, 141/18, 301, 302, 363–367, 351–356; 128/200.14–200.23; 137/614.01–614.06

See application file for complete search history.

(56) References Cited

U.S. PATENT DOCUMENTS

| 5,687,777 | A | * | 11/1997 | Dobson et al. ............... 141/18 |
| 5,758,640 | A | * | 6/1998 | Kamppari et al. ..... 128/202.27 |
| 5,915,427 | A | * | 6/1999 | Grabenkort ................. 141/364 |
| 6,158,486 | A | * | 12/2000 | Olson et al. ................. 141/351 |
| 6,390,156 | B1 | * | 5/2002 | Hetherington et al. ...... 141/351 |
| 6,585,016 | B1 | | 7/2003 | Falligant et al. |
| 6,929,041 | B2 | * | 8/2005 | Falligant et al. ............ 141/351 |
| 7,168,467 | B2 | * | 1/2007 | Turker et al. ................ 141/292 |

* cited by examiner

*Primary Examiner*—Steven O. Douglas
(74) *Attorney, Agent, or Firm*—McGlew and Tuttle, P.C.

(57) ABSTRACT

The interaction between a filling valve (28) on the filling device and an adapter valve on a bottle adapter has improved anesthetics filling features including radially inwardly directed bars (26), which engage (pass into) corresponding slots on the outlet pipe of the bottle adapter. The bars engaged in the slots actuate the adapter valve. The bars are provided on the inner wall of a filler neck (22).

14 Claims, 4 Drawing Sheets

FILLING SYSTEM FOR AN ANESTHETIC EVAPORATOR

CROSS REFERENCE TO RELATED APPLICATIONS

This application claims the benefit of priority under 35 U.S.C. § 119 of German Patent Application DE 10 2004 063 883.7 filed Dec. 21, 2004, the entire contents of which are incorporated herein by reference.

FIELD OF THE INVENTION

The present invention pertains to a filling system for an anesthetic evaporator.

BACKGROUND OF THE INVENTION

A filling system of the type mentioned has become known from U.S. Pat. No. 6,585,016 B1. To make it possible to fill liquid anesthetic into an anesthetic evaporator, a bottle adapter is necessary, which establishes the connection between the storage container for liquid anesthetic and the filling device at the anesthetic evaporator. A collet, which has two grooves for receiving an index collar arranged at the neck of the storage container, is provided at the bottle-side end of the bottle adapter. The index collar has an anesthetic-specific design, so that only the bottle adapter fitting the storage container can be screwed on the thread of the bottle.

An anesthetic-specific coding in the form of two projections, which are arranged offset in relation to one another at an angle and which engage corresponding openings on the filler neck of the filling device, is likewise provided at the neck of the bottle adapter.

The outlet pipe of the bottle adapter is closed by means of a spring-loaded adapter valve, so that no anesthetic vapor can escape into the environment. A corresponding filling valve is provided at the filling device. A stationary bar, whose length is selected to be such that the adapter valve can be opened when the adapter neck is introduced into the filler neck of the filling device, is located in the middle of the filler neck. The interaction between the bottle adapter and the filling device is designed such that the filling valve opens first and the adapter valve opens thereafter. Liquid anesthetic can then flow from the storage container into the tank of the anesthetic evaporator.

The drawback of the prior-art filling system is that the stationary bar, with which the adapter valve is opened, and the filling valve are connected to one another as one assembly unit and can therefore mutually affect each other. In addition, the design of the valve is relatively complicated.

SUMMARY OF THE INVENTION

The basic object of the present invention is to simplify a filling system of the type mentioned in terms of its design and to improve the interaction between the filling valve and the adapter valve.

According to the invention, a filling system is provided for an anesthetic evaporator. The filling system includes a bottle adapter for being connected to a storage container for liquid anesthetic. The bottle adapter has an adapter neck and an outlet pipe with a slot extending in a longitudinal direction of the bottle adapter. An adapter valve is provided on the outlet pipe of the bottle adapter. The adapter valve has an actuating surface with the adapter valve being brought from a closed position into an open position via the actuating surface. A first anesthetic-specific coding is provided on the adapter neck. A filling device for filling anesthetic at the anesthetic evaporator is provided having a filler neck for receiving the adapter neck. A filling valve is provided with a valve plate in the filling device, the valve plate being brought from a closed position into an open position by the outlet pipe of the bottle adapter. A second anesthetic-specific coding is provided on the filler neck, the second anesthetic-specific coding having a design corresponding to the first anesthetic-specific coding. A bar extends from the inner wall of the filler neck at a right angle to a direction of flow of the anesthetic, the bar engaging the slot to be caused to engage the actuating surface of the adapter valve by pressing the bottle adapter relative to the filling device.

According to another aspect of the invention, a filling system is provided for an anesthetic evaporator. The filling system includes a bottle adapter having an adapter neck and an adapter pipe with a slot extending in the longitudinal direction. An adapter valve is provided on (connected to) the adapter pipe, the adapter valve being brought from a closed position into an open position via an actuating surface in the area of the slot. A filling device is provided on the anesthetic evaporator with a filler neck for receiving the adapter neck and with a filling valve. A bar is attached to the filler neck and extends radially toward a center thereof. The bar engages the slot and engages the actuating surface of the adapter valve.

The advantage of the present invention is essentially that the opening mechanisms for the adapter valve and the filling valve are completely uncoupled. Instead of a centrally arranged, stationary bar, which is passed through the filling valve at the filling device, at least one stationary bar, which actuates the adapter valve via a laterally longitudinally extending slot or a plurality of slots at the outlet pipe of the bottle adapter, is arranged at the inner wall of the filler neck. It is thus possible to design especially the filling valve as a simple lifting valve, which is not compromised by additional functions. In addition, it is possible to cover the front side of the outlet pipe in order to prevent the adapter valve from being damaged. Due to the arrangement according to the present invention of a stationary bar, which is attached to the inner wall of the filler neck and points radially toward the center of the filler neck, only a longitudinally extending slot, which can be engaged by the bar in order to actuate the adapter valve, needs to be provided at the outlet pipe of the bottle adapter. The outlet pipe can thus have an especially robust design in order to protect the adapter valve against possible damage.

The anesthetic-specific coding is advantageously designed as a polygon. For example, a hexagon may thus be selected as the polygon for the anesthetic halothane, a regular pentagon for enflurane, and a regular heptagon for isoflurane. Thus, no special preferred position is to be complied with for introducing the bottle adapter into the filling device, but the introduction position can be found by slightly rotating the bottle adapter in relation to the filling device. An outer polygon is located on the bottle adapter, and an inner polygon, into which the outer polygon can be introduced like a wrench, is arranged within the filler neck.

It is especially advantageous to design the bar as a spoked wheel and to provide corresponding slots on the outlet pipe of the bottle adapter corresponding to the spoked wheel. The spoked wheel comprises individual bars, which are directed toward the center of the filler neck. As an alternative to the polygon or even in addition to the polygon, an anesthetic-specific coding can be embodied by selecting the number of bars in the spoked wheel or by selecting their angular positions in relation to one another. The fact that the valve piston of the adapter valve is lifted uniformly is also an advantage of a spoked wheel compared to an individual bar.

Connecting the bottle adapter rigidly to the storage container for liquid anesthetics is also within the scope of the present invention.

An exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
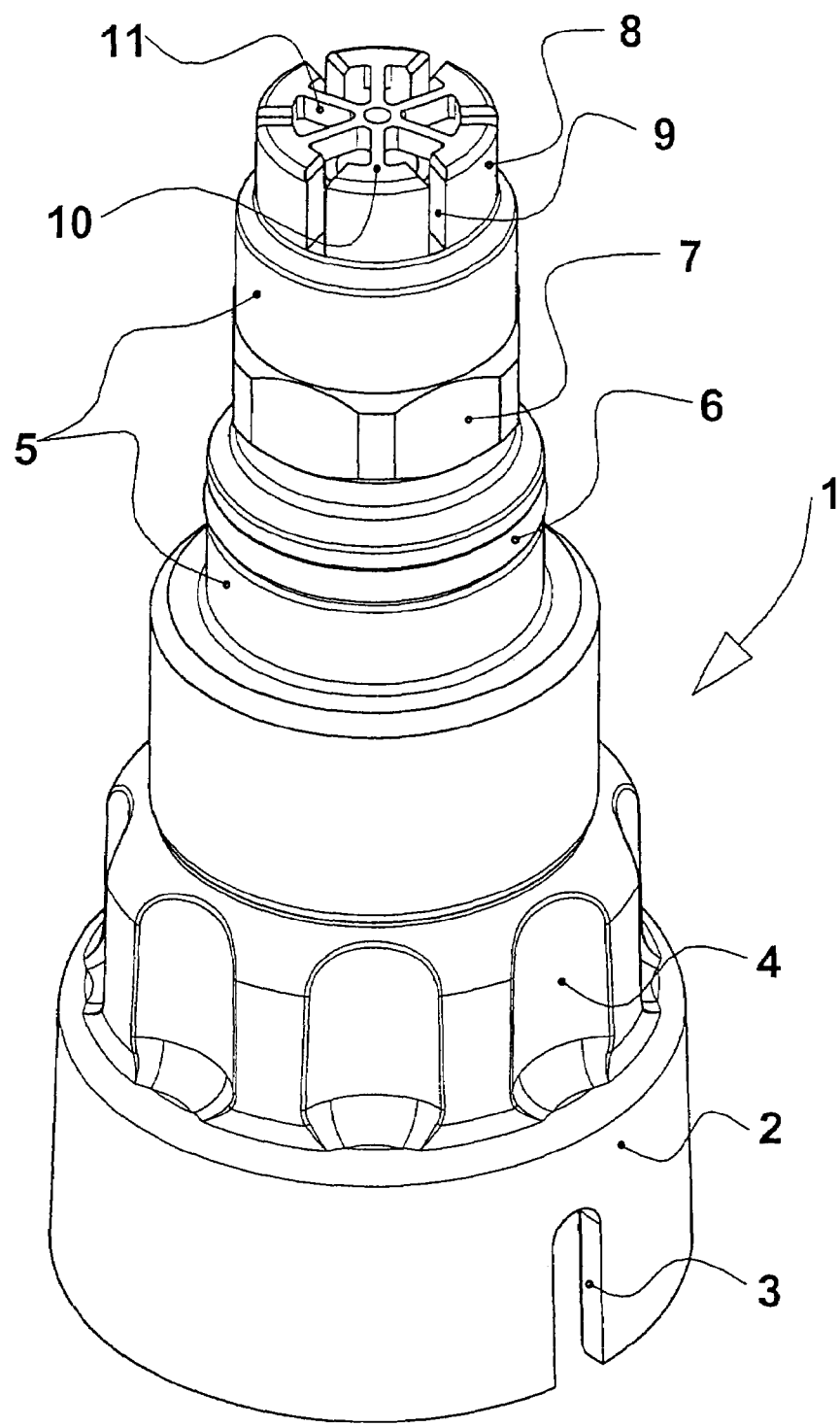
FIG. 1 is a perspective view of a bottle adapter.

Referring to the drawings in particular, FIG. 1 shows a perspective view of a bottle adapter 1, which has a collet 2 on its underside for being screwed onto a storage container for liquid anesthetic, not shown in greater detail in FIG. 1. On its bottle collar, the storage container has an anesthetic-specific index collar, which is introduced into receiving grooves 3 of the collet 2. Thus, only a bottle adapter 1 that belongs to the anesthetic can be screwed onto the storage container. The screwing movement is facilitated by recessed grips 4 above the collet 2. An adapter neck 5 with an O-ring 6 and with an outer polygon 7 for the anesthetic-specific coding as well as an outlet pipe 8 with radially extending slots 9 are located at the top end of the bottle adapter 1. The top side 10 of the pipe is designed as a star 11.

Figure 2:
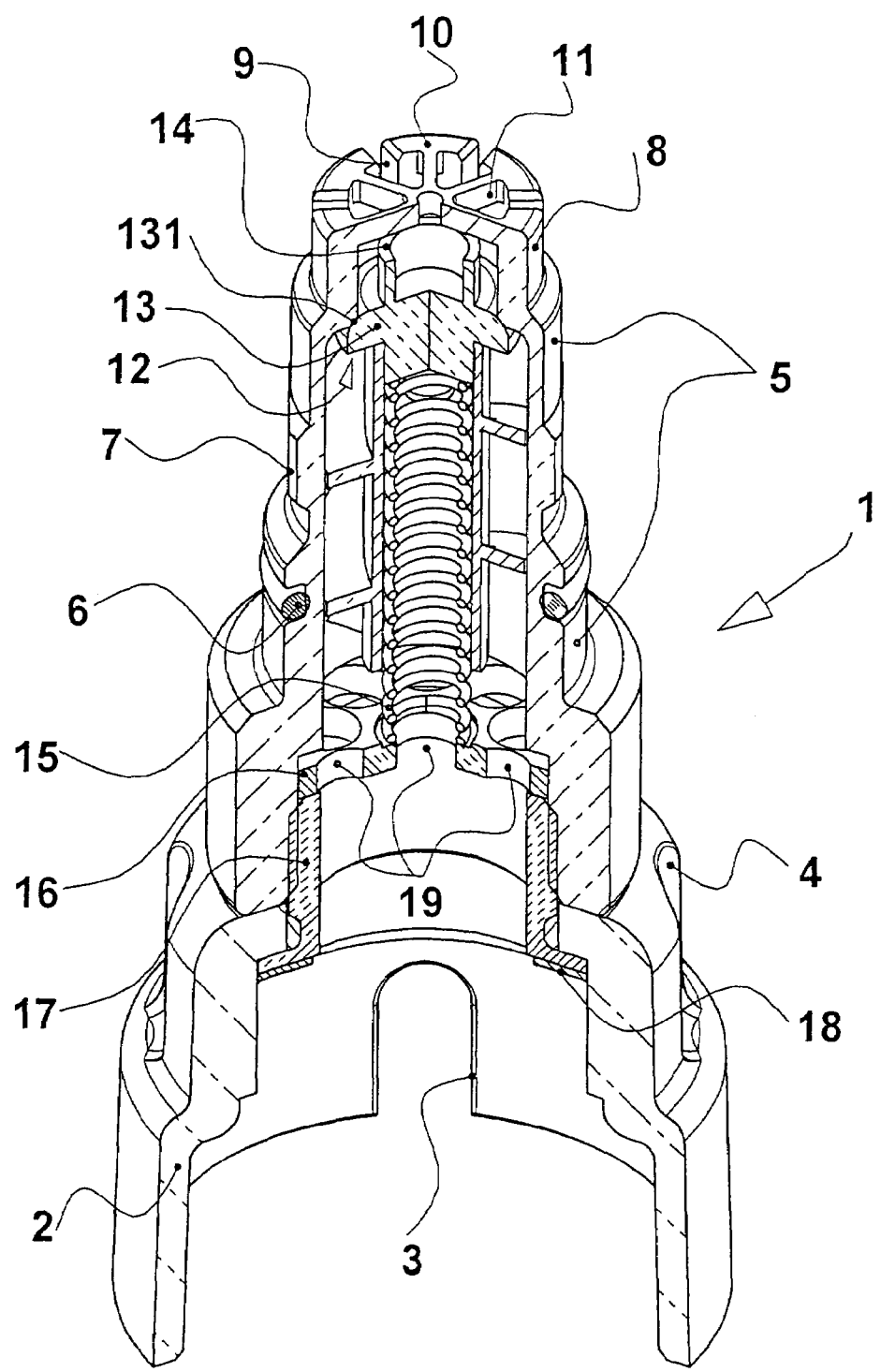
FIG. 2 is a longitudinal sectional view through the bottle adapter according to FIG. 1.

FIG. 2 illustrates the longitudinal view of the bottle adapter 1 according to FIG. 1. Identical components are designated by the same reference numbers as in FIG. 1. A shut-off valve 12 with a valve piston 13, a ring 14 on the top side of the valve piston 13 and with a valve spring 15, which is pretensioned by means of a support plate 16 and presses the valve piston 13 against a sealing surface 131, is located within the bottle adapter 1. The support plate 16 is held within the bottle adapter 1 by a support cage 17. A sealing washer 18, which is in contact with the bottle neck of the storage container, not shown in the figures, is attached to the underside of the support cage 17. The support plate 16 contains holes 19, via which the exchange of gas and liquid takes place. The polygon 7 has an anesthetic-specific design, for example, a hexagon polygon 7 is designed in an anesthetic-specific manner, for example, a hexagon for halothane, a regular pentagon for enflurane, and a regular heptagon for isoflurane.

Figure 3:
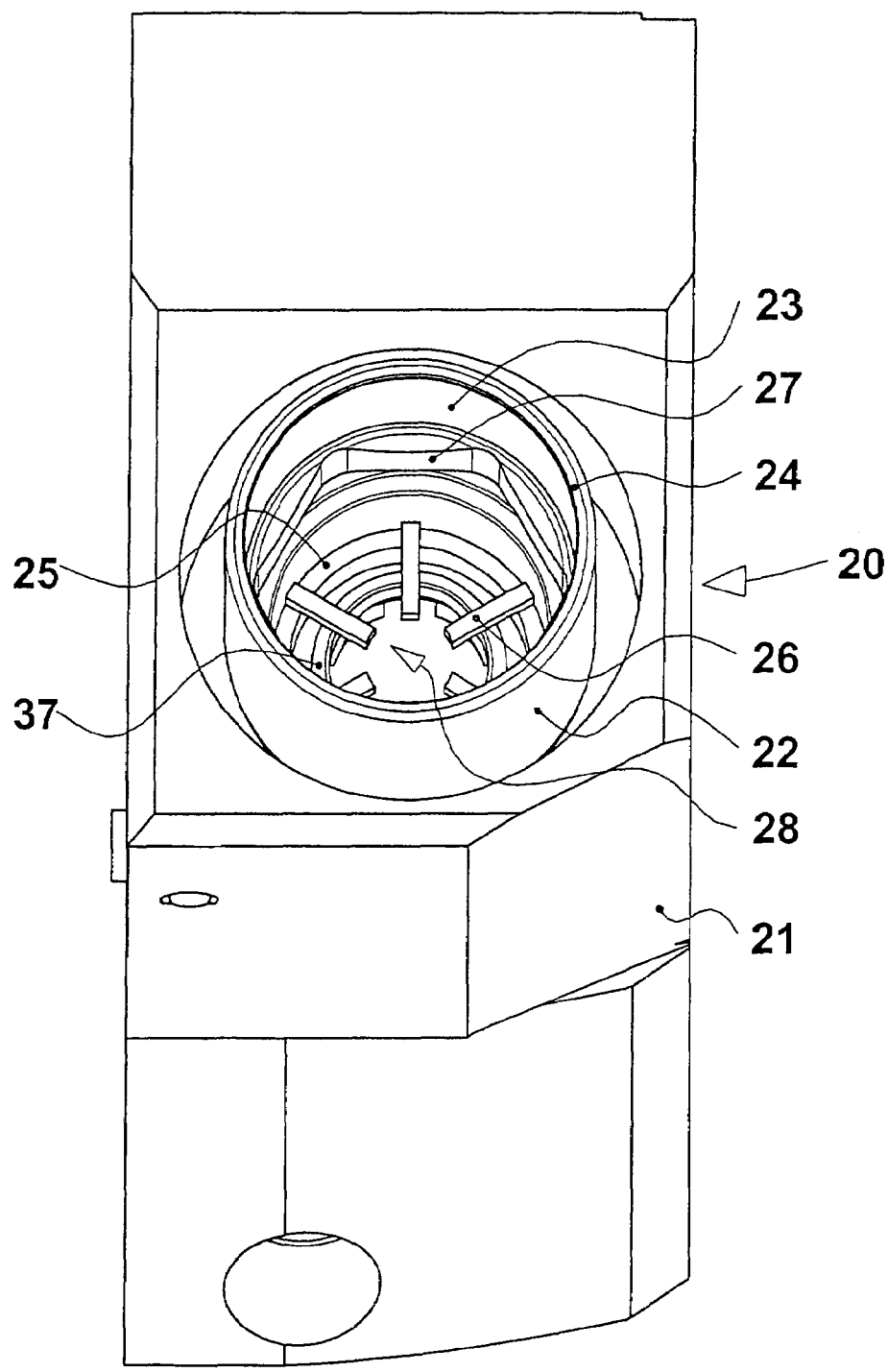
FIG. 3 is a perspective view of a filling device.

FIG. 3 shows a perspective view of a filling device 20 for anesthetics at an anesthetic evaporator 21. The filling device 20 has a filler neck 22 with a cylindrical sealing surface 23, an inner lead-in bevel 24 on the upper part of the filler neck 22, a spoked wheel 25 with radially inwardly pointing bars 26, an inner polygon 27 for the anesthetic-specific coding, and a filling valve 28.

Figure 4:
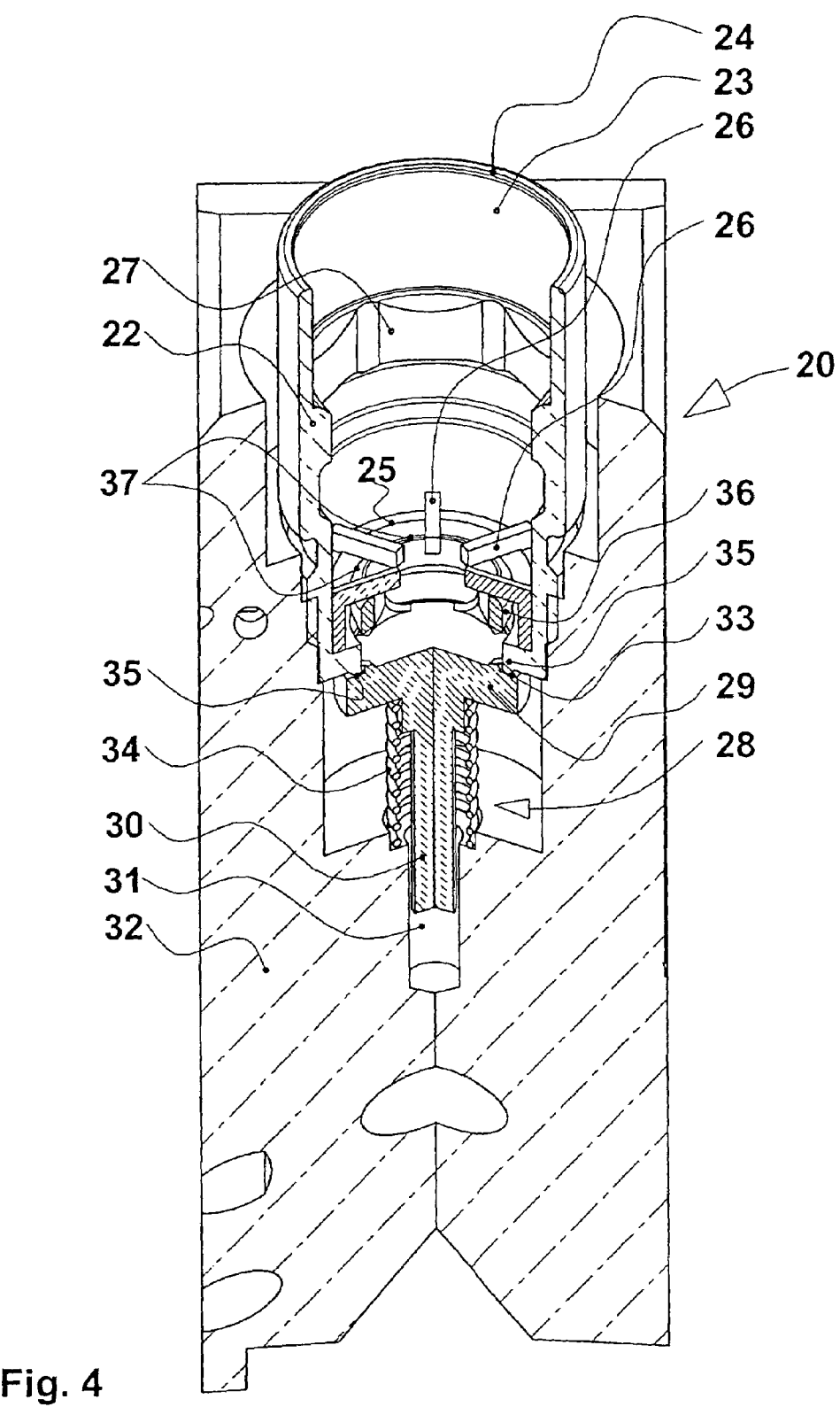
FIG. 4 is a longitudinal section through the filling device according to FIG. 3.

FIG. 4 shows the longitudinal section of the filling device 20. Identical components are designated by the same reference numbers as in FIG. 3. The filling valve 28 comprises a valve plate 29 at a valve guide bar 30, which is accommodated in a hole 31 of the evaporator housing 32 in such a way that it can perform lifting movements. The top side 33 of the valve plate 29 is pressed by means of a valve spring 34 against a sealing crater 35 of the filling valve 28. A guide ring 36 is connected with the valve plate 29 and is displaceable together with the valve plate 29.

The filling system according to the present invention operates as follows:

When the bottle adapter 1 is plugged into the filling device 20, the O-ring 6 will first slide over the lead-in bevel 24 and will come into contact with the sealing surface 23 of the filler neck 22. Later, the outer polygon 7 will engage the inner polygon 27 and the bottle adapter 1 will be centered in relation to the filling device 20 as a result. The bars 26 will then be located in the slots 9 of the outlet pipe 8 and the outlet pipe 8 will enter the area of the guide ring 36.

By pressing the bottle adapter 1, the top side 10 of the pipe of the bottle adapter comes into contact with the top side 37 of the guide ring 36 and the filling valve 28 will open. The adapter valve 12 is still closed. If the pressure on the bottle adapter 1 is increased further, the valve plate 29 is displaced farther downward against the force of the valve spring 34 and the bars 26 will touch the ring 14 of the valve body 13, as a result of which the adapter valve 12 will open. Anesthetic will now flow from the storage container via the holes 19 of the support plate 16 into the tank of the anesthetic evaporator, and, as in communicating vessels, gas will flow back from the tank into the storage container via the holes 19.

When the filling operation is finished, the adapter valve 12 will close first, so that residual quantities of anesthetic that may be present within the filler neck 22 can flow off into the tank of the anesthetic evaporator 21. The filling valve 28 is then closed and the bottle adapter 1 can be removed from the filler neck 22.

While a specific embodiment of the invention has been shown and described in detail to illustrate the application of the principles of the invention, it will be understood that the invention may be embodied otherwise without departing from such principles.

What is claimed is:

1. A filling system for an anesthetic evaporator, the filling system comprising:

a bottle adapter for being connected to a storage container for liquid anesthetic, said bottle adapter having an adapter neck and an outlet pipe with a slot extending in a longitudinal direction of said bottle adapter;

an adapter valve on said outlet pipe of said bottle adapter, said adapter valve having an actuating surface with said adapter valve being brought from a closed position into an open position via said actuating surface;

a first anesthetic-specific coding on said adapter neck;

a filling device for filling anesthetic at the anesthetic evaporator, said filling device having a filler neck for receiving said adapter neck;

a filling valve with a valve plate in said filling device, said valve plate being brought from a closed position into an open position by said outlet pipe of said bottle adapter;

a second anesthetic-specific coding on said filler neck, said second anesthetic-specific coding having a design corresponding to said first anesthetic-specific coding; and a bar extending radially from the inner wall of said filler neck, said bar engaging said slot to be caused to engage said actuating surface of said adapter valve by pressing said bottle adapter relative to said filling device.

2. A filling system in accordance with claim 1, wherein said first anesthetic-specific coding is designed as a polygon.

3. A filling system in accordance with claim 1, further comprising additional bars extending from an inner wall of said filler neck at a right angle to a direction of flow of the anesthetic wherein said bar and said additional bars form spokes of a spoked wheel and additional slots are provided cooperating with said slot whereby said slots are designed corresponding to said spoked wheel at said outlet pipe of said bottle adapter.

4. A filling system for an anesthetic evaporator, the filling system comprising:
   a bottle adapter having an adapter neck and an adapter pipe with a slot extending in the longitudinal direction;
   an adapter valve on said adapter pipe, said adapter valve being brought from a closed position into an open position via an actuating surface in the area of said slot;
   a filling device with a filler neck for receiving said adapter neck and with a filling valve; and
   a bar attached to said filler neck and extending radially toward a center thereof, said bar engaging said slot and engaging said actuating surface of said adapter valve.

5. A filling system in accordance with claim 4, wherein said bar is attached to an inner wall of said filler neck at right angles to the direction of flow of the anesthetic.

6. A filling system in accordance with claim 4, further comprising additional bars extending from an inner wall of said filler neck at a right angle to a direction of flow of the anesthetic and additional slots cooperating with said slot wherein said bar and said additional bars form spokes of a spoked wheel and said slots are designed corresponding to said spoked wheel at said outlet pipe of said bottle adapter.

7. A filling system in accordance with claim 4, wherein said bottle adapter is rigidly connected to said storage container.

8. A filling system in accordance with claim 4, further comprising:
   an adapter anesthetic-specific coding on said adapter neck;
   a filler neck anesthetic-specific coding on said filler neck, said filler neck anesthetic-specific coding having a design corresponding to a first anesthetic-specific coding.

9. A filling system in accordance with claim 8, wherein each said anesthetic-specific coding comprises surface portions defining a polygon.

10. An anesthetic filling system comprising:
    a storage container containing anesthetic and having an adapter neck with a connected adapter pipe and with radial slots having a depth extending in the longitudinal direction of the adapter pipe;
    anesthetic evaporator having an anesthetic reservoir and a filling device for filling said reservoir, said filling device having a filler neck for receiving said adapter neck;
    an adapter valve connected to said outlet pipe, said adapter valve having an actuating surface in the area of said slots, said adapter valve being brought from a closed position into an open position via movement of said actuating surface;
    a filling valve connected to said filling device; and
    radially extending bars attached to said filler neck, said bars extending into respective said slots and engaging said actuating surface of said adapter valve for actuating said adapter valve.

11. A filling system in accordance with claim 10, wherein said bar is attached to an inner wall of said filler neck at right angles to the direction of flow of the anesthetic.

12. A filling system in accordance with claim 10, wherein said bottle adapter is rigidly connected to said storage container.

13. A filling system in accordance with claim 10, further comprising:
    an adapter anesthetic-specific coding on said adapter neck;
    a filler neck anesthetic-specific coding on said filler neck, said filler neck anesthetic-specific coding having a design corresponding to a first anesthetic-specific coding.

14. A filling system in accordance with claim 13, wherein each said anesthetic-specific coding comprises surface portions defining a polygon.

* * * * *